United States Patent
Manhart

(10) Patent No.: US 11,166,689 B1
(45) Date of Patent: Nov. 9, 2021

(54) PROVIDING A DYNAMIC MASK IMAGE

(71) Applicant: Siemens Healthcare GmbH, Erlangen (DE)

(72) Inventor: Michael Manhart, Fürth (DE)

(73) Assignee: Siemens Healthcare GmbH, Erlangen (DE)

( * ) Notice: Subject to any disclaimer, the term of this patent is extended or adjusted under 35 U.S.C. 154(b) by 0 days.

(21) Appl. No.: 17/235,317

(22) Filed: Apr. 20, 2021

(30) Foreign Application Priority Data

Apr. 21, 2020 (DE) ...................... 10 2020 205 039.2

(51) Int. Cl.
*A61B 6/00* (2006.01)
(52) U.S. Cl.
CPC ............ *A61B 6/5235* (2013.01); *A61B 6/481* (2013.01); *A61B 6/501* (2013.01); *A61B 6/503* (2013.01)
(58) Field of Classification Search
CPC ....... A61B 6/504; A61B 6/481; A61B 6/4441; A61B 6/5235; A61B 6/503; A61B 6/501; G06T 2207/30101; G06T 2207/10116
See application file for complete search history.

(56) References Cited

U.S. PATENT DOCUMENTS

2011/0037761 A1  2/2011  Mistretta et al.
2013/0237815 A1  9/2013  Klingenbeck

FOREIGN PATENT DOCUMENTS

DE    102012203751 A1    9/2013

OTHER PUBLICATIONS

German Decision to Grant for German Application No. 10 2020 205 039.2 decision dated Mar. 22, 2021, with English translation.
German Office Action for German Application No. 10 2020 205 039.2 dated Feb. 17, 2021, with English translation.

*Primary Examiner* — Courtney D Thomas
(74) *Attorney, Agent, or Firm* — Lempia Summerfield Katz LLC

(57) ABSTRACT

A computer-implemented method and system for providing a dynamic mask image, including receiving projection images that image an examination region containing at least one vessel from at least two different projection directions, receiving a static mask image, initializing the dynamic mask image, determining exclusive rays that extend in each case parallel to one of the projection directions and correspond to a respective image value in the associated projection image, wherein at least one of the exclusive rays in each case extends through precisely one of the unmasked image areas of the static mask image, identifying and masking contrasted and uncontrasted vessels in the static mask image, annotating the contrasted and uncontrasted vessels in the dynamic mask image, determining and masking an imaging of the contrasted vessels in the projection images, repeating certain steps until an abort condition occurs, and providing the dynamic mask image.

20 Claims, 6 Drawing Sheets

PROVIDING A DYNAMIC MASK IMAGE

CROSS REFERENCE TO RELATED APPLICATIONS

This application claims the benefit of DE 102020205039.2, filed on Apr. 21, 2020 which is hereby incorporated by reference in its entirety.

FIELD

Embodiments relates to a computer-implemented method for providing a dynamic mask image.

BACKGROUND

Physiologically accurate imaging of an examination region, for example a head and/or heart region, is often necessary for a successful diagnosis and/or treatment of an examination subject. In such cases the examination subject may be a human and/or animal patient and/or a flow phantom, for example. For example, in order to visualize a blood flow dynamic in the examination region, the examination subject is routinely given contrast agents whose degree of contrast enhancement may be imaged visibly and dynamically with respect to time by an, for example angiographic, imaging modality. A frequent disadvantageous aspect is spatially overlapping vessel segments in the examination region, that may lead, for example, in the case of projection images, to ambiguities in terms of the respective degree of contrast enhancement.

Known methods, for example heuristic ("trial and error" algorithms) and/or exhaustion-based ("brute force" algorithms), for determination of the degrees of contrast enhancement of vessels often require a high computational overhead that increases exponentially with the number of vessels.

BRIEF SUMMARY AND DESCRIPTION

The scope of the present invention is defined solely by the appended claims and is not affected to any degree by the statements within this summary. The present embodiments may obviate one or more of the drawbacks or limitations in the related art.

Embodiments provide a reliable and at the same time computationally efficient determination of a degree of contrast enhancement of vessels in an examination region of an examination subject.

Embodiments include a computer-implemented method for providing a dynamic mask image. The method includes, in a first step S1.1), receiving projection images of an examination region of an examination subject. The projection images image the examination region from at least two different projection directions. In a second step S1.2), a static mask image is received. The examination region contains at least one vessel that is imaged by an unmasked area of the static mask image. In a third step S1.3), the dynamic mask image is initialized by the static mask image. In a fourth step S3), exclusive rays are determined. At this stage, the exclusive rays in each case extend in a ray incidence direction with respect to one of the projection directions and correspond to a respective image value in the associated projection image. Furthermore, at least one of the exclusive rays extends in each case through precisely one of the unmasked image areas of the static mask image. In a fifth step S4.1), contrasted and uncontrasted vessels are identified based on the corresponding image value. In a sixth step S4.2), the vessels identified in step S4.1) are masked in the static mask image. In a seventh step S4.3), the contrasted and uncontrasted vessels are annotated in the dynamic mask image. In an eighth step S.5), an image of the contrasted vessels identified in step S4.1) is determined and masked in the projection images. Steps S3) to S5) may be performed repeatedly until an abort condition occurs. When the abort condition occurs, the dynamic mask image is provided in a ninth step S7).

The receiving of the projection images in step S1.1) and/or the receiving of the static mask image in step S1.2) may include, for example, an acquisition and/or readout of a computer-readable data memory and/or a receiving from a data storage unit, for example a database. The projection images and/or the static mask image may be provided by a provisioning unit of a medical imaging device. For example, the projection images and the static mask image may be provided by a single medical imaging device or by different medical imaging devices, for example by the provisioning units thereof.

The projection images may for example be two-dimensional. Advantageously, the projection images may image the examination region from the at least two different spatial projection directions, for example angulations. The projection images may in this case include for example X-ray projection images and/or ultrasound images and/or positron emission tomography images. Moreover, the projection images may image the examination region at least one, for example every, acquisition time point of the projection images from at least two projection directions in each case. A change with respect to time affecting the examination region may be provided, for example a propagation movement of a contrast agent and/or a movement of a medical object, at the at least one acquisition time point of the projection images is imaged from at least two projection directions. The projection images include a common imaging area of the examination region, at least in pairs. Furthermore, the projection images may be temporally resolved, for example at least in pairs. Moreover, the projection images may image the examination region from more than two different projection directions at least one common acquisition time point, for example simultaneously. Furthermore, the projection images and/or the static mask image may include metadata, the metadata possibly including for example information in relation to an acquisition parameter and/or operating parameter of the medical imaging device.

The examination region of the examination subject may contain at least one vessel, for example a vessel segment and/or a vessel structure and/or a vessel tree. In this case the examination region may be for example an anatomical region of the examination subject, for example a head region and/or heart region. The at least one vessel may be for example a blood vessel, for example an artery and/or vein, and/or a hollow organ.

The static mask image may be two-dimensional and/or three-dimensional. Furthermore, the static mask image may contain an unmasked and/or a masked image area. The at least one vessel may be imaged by an unmasked image area of the static mask image. Furthermore, a masked image area of the static mask image may for example image a tissue background and/or an anatomical section of the examination region, which anatomical section is not a vessel. For example, the static mask image may be generated by segmentation of the at least one vessel in an, for example two-dimensional and/or three-dimensional, image of the examination region. For example, the static mask image may have been generated from a reconstruction image, for example a three-dimensional reconstruction image, that has been reconstructed from the projection images. Alternatively, or in addition, the static mask image may be based on a planning dataset, for example one that has been acquired preoperatively. The static mask image may for example include a binary differentiation into masked and unmasked image areas. The static mask image may include image elements, for example pixels and/or voxels, with each image element including an image value. Masked and unmasked image areas may be distinguishable for example in respect of a threshold value based on the image values of the static mask image.

The static mask image for initializing the dynamic mask image may be specified in step S1.3). The dynamic mask image may for example include all characteristics and features that are described in relation to the static mask image.

The projection images may in each case contain a plurality of ray incidence directions in respect of the respective projection direction. In this case the projection direction may for example describe a spatial ray, for example a central ray, between an imaging source, for example an X-ray source and/or an ultrasound transmitter, and a detector. Furthermore, the ray incidence directions may extend in parallel and/or in a fan shape and/or in a cone shape in respect of the projection direction, for example by a parallel ray and/or a cone beam and/or a fan beam in the case of a projection image. Each of the projection images may include a plurality of image elements, for example pixels and/or voxels, one of the image elements in each case corresponding to an imaging of the examination region along one of the ray incidence directions. Furthermore, each of the image elements of the projection images may have an image value that corresponds to an absorption value and/or an intensity value and/or an attenuation value, of an imaging along the respective ray incidence direction.

Exclusive rays may be determined in step S3). An exclusive ray in this context may be a spatial ray along one of the ray incidence directions that corresponds to one of the at least two projection directions, the exclusive ray extending through precisely one of the unmasked image areas, for example a vessel imaged by the unmasked image area, of the static mask image. Step S3) may for example include a check for the presence of exclusive rays in the static mask image. If no exclusive ray may be determined in the static mask image in step S3), the abort condition may be checked directly, for example steps S4.1) to S5) being omitted in this case.

If at least one exclusive ray may be determined in step S3), the at least one exclusive ray may have a corresponding image value in the associated projection image. In this case the corresponding image value may correspond to an image element that is imaged by a projection along the exclusive ray. Because the at least one exclusive ray extends through precisely one unmasked image area of the static mask image, the corresponding image value is based on a projection of the vessel imaged by the unmasked image area along the exclusive ray. For example, the corresponding image value contains no contributions from other unmasked image areas of the static mask image, for example no contributions of further vessels imaged thereby.

In step S4.1), contrasted and uncontrasted vessels in the examination region may be identified based on the corresponding image value in each case. In this context the degree of contrast enhancement of a vessel may describe for example a fill state of the vessel with a contrast agent, for example one that is X-ray-opaque, at the acquisition time point of the respective projection image. Contrasted vessels may be for example vessels that were filled, at least partially, with a contrast agent at the acquisition time point of the respective projection image. Analogously thereto, uncontrasted vessels may be for example vessels that have no at least partial filling with a contrast agent at the acquisition time point of the respective projection image. Furthermore, the identifying of the contrasted and/or uncontrasted vessels based on the respective corresponding image value may include a classification, for example a differentiation. In this case the classification may be carried out for example based on a comparison of the corresponding image values with a threshold value. The threshold value may for example specify an absorption value and/or attenuation value and/or intensity value, with the respective vessel being at least partially filled, for example contrasted, when the threshold value is reached and/or exceeded by a corresponding image value.

At least some of the vessels imaged by the unmasked image areas in the static mask image may therefore be identified in step S4.1), for example on the basis of the exclusive rays and the image values corresponding thereto.

The vessels identified as contrasted and/or un-contrasted in step S4.1) that are imaged in the static mask image by unmasked image areas, may be masked in step S4.2). The unmasked image areas by which the identified vessels in the static mask image are imaged, for example equivalently, are aligned to the remaining masked image areas of the static mask image. In this case the unmasked image areas by which the identified vessels are imaged in the static mask image may be converted into masked image areas, for example by a change in the image values of the respective unmasked image areas. Thus, after step S4.2), the static mask image now contains only the unmasked image areas by which vessels are imaged that could not be identified in step S4.1).

In step S4.3), the contrasted and un-contrasted vessels that were identified in step S4.1) may be annotated in the dynamic mask image. The annotation of the contrasted and uncontrasted vessels may for example include a marking and/or characterization of unmasked image areas of the dynamic mask image, by which unmasked image areas the contrasted and uncontrasted vessels are imaged. Alternatively, or in addition, the annotation may include a change in image values in the unmasked image areas as a function of the degree of contrast enhancement of the vessels identified in step S4.1), by which unmasked image areas the identified vessels are imaged. For example, a first image value range may be specified for the contrasted vessels, and a second image value range for the uncontrasted vessels. Moreover, a third image value range may be specified in addition for the masked image areas of the dynamic mask image. The annotation in step S4.3) may be carried out in such a way that the image values of the image elements that the respective, for example spatially demarcated, unmasked image area, by which unmasked image area a vessel identified in step S4.1) is imaged, are adjusted in accordance with the degree of contrast enhancement of the identified vessel. Accordingly, for example all image values of the image elements in an unmasked image area of the dynamic mask image in each case may be annotated, for example adjusted, based on the degree of contrast enhancement of the associated vessel.

In step S5), an image of the contrasted vessels identified in step S4.1) may furthermore be determined in the projection images. The imaging of the identified contrasted vessels may for example include a plurality of image elements each having an image value. In this case the image values of the image elements may be determined for example by a forward projection along the projection direction, which projection direction corresponds to the respective projection image. In this case the imaging of the identified contrasted vessels may include only the contrasted vessels identified in step S4.1), and no further, for example remaining, vessels, which further vessels are imaged by unmasked image areas of the static mask image.

If at least two contrasted vessels are identified in step S4.1), in which case the unmasked image areas corresponding to the at least two contrasted vessels overlap along at least one of the projection directions, the imaging of the at least two contrasted vessels along the at least one projection direction may include an overlay. Furthermore, the imaging of the identified contrasted vessels determined in step S5) may be masked in the projection images. In this case the masking of the imaging in the projection images may include for example a multiplication and/or subtraction of image values. Contributions of the identified contrasted vessels to the image values of the projection images may be masked, for example removed. Accordingly, after step S5), the projection images contain only contributions of vessels that were not identified in step S4.1).

Uncontrasted vessels may make substantially no contribution to the image values of the projection images. If the uncontrasted vessels make at least a small contribution to the image values of the projection images, step S5) may additionally include a masking of the imaging of the uncontrasted vessels identified in step S4.1) in the projection images.

Steps S1.1) and S1.2) may be performed in any order relative to one another and/or simultaneously. Steps S4.2), S4.3) and/or S5) may also be performed in any order relative to one another and/or simultaneously.

Furthermore, steps S3) to S5) may be performed repeatedly until the abort condition occurs. Here, the static mask image annotated and/or masked in steps S4.2) and S4.3) and/or the dynamic mask image may be provided in the case of the repeated execution starting from step S3). Analogously thereto, the projection images masked in step S5) may be provided in the case of the repeated execution starting from step S3).

A number of unmasked image areas in the static mask image may be reduced with each iteration of steps S3) to S5). This provides a computational overhead for the identification of contrasted and uncontrasted vessels to be reduced in the respective following iteration. For example, the vessels corresponding to the unmasked image areas may be identified in the dynamic mask image and annotated in accordance with their degree of contrast enhancement. In other words, a problem in relation to the identification of the degree of contrast enhancement of the vessels imaged by the unmasked image areas in the static or dynamic mask image may be reduced with each iteration of steps S3) to S5).

The abort condition may for example include a maximum number of iterations and/or a minimum number of exclusive rays in step S3) and/or a minimum number of unmasked image areas in the static mask image. If no exclusive rays may be determined in step S3) and the static mask image includes at least one unmasked image area, the degree of contrast enhancement of the vessels imaged thereby may be identified for example by artificial intelligence and/or based on an empirical method, for example a brute-force approach.

Step S7) may be performed after the abort condition occurs. The, for example most recently, annotated dynamic mask image may be provided in step S7). Providing the dynamic mask image may for example include storing the same on a computer-readable storage medium and/or displaying the same on a visualization unit and/or transferring the same to a provisioning unit. For example, a graphical representation of the dynamic mask image may be displayed on the visualization unit.

Determining the exclusive rays in step S3) provides for the vessels that are unequivocally identifiable on the basis of the corresponding image values to be identified in each case, masked in the static mask image and annotated in the dynamic mask image. Accordingly, a computationally efficient identification of the degree of contrast enhancement of the individual vessels may be made possible even in the case of complex arrangements of vessels in the examination region.

In an embodiment of the computer-implemented method for providing a dynamic mask image, the method may additionally include steps S2.1) to S2.4). In this case a minimum image may be determined in step S2.1) based on the projection images. Uncontrasted and potentially contrasted vessels in the minimum image may be identified in a step S2.2). In a step S2.3), the uncontrasted vessels may be masked in the static mask image. In addition, in a step S2.4), the uncontrasted vessels may be annotated in the dynamic mask image.

The minimum image may be for example two-dimensional and/or three-dimensional. For example, the minimum image may possess the same dimensionality as the static mask image. Furthermore, the minimum image may include a plurality of image elements each including an image value. In this case the image elements may be determined, for example spatially, by in each case at least two image elements of the projection images of different projection directions. The image elements of the minimum image may be determined, for example spatially, by an image element of one of the projection images in each case along the at least two different projection directions. Furthermore, the image values of the image elements of the minimum image may be based on the image values of the associated image elements of the projection images. For example, an image value of an image element of the minimum image may be assigned an image value of an image element of a projection image along one of the projection directions. In this case the assignment of the image value may be based on a comparison of the image elements corresponding to the image element of the minimum image, for example the image values, of the projection images. The minimum image may be determined for example by applying a minimum intensity projection of the projection images along the different projection directions. Thus, the image values of the minimum image may have in each case the minimum of the associated image values of the projection images along the different projection directions.

The examination region, for example the at least one vessel, is imaged by the image elements of the minimum image. The image elements of the minimum image that correspond to the at least one vessel, may be identified on the basis of the static mask image. Based on the image values of the identified image elements in the minimum image, the uncontrasted vessels may be identified first in step S2.2). In this case a contrast threshold value may be specified in respect of the image values of the minimum image, image values below the threshold value corresponding to an uncontrasted vessel. The contrast threshold value may for example specify an absorption value and/or an intensity value and/or an attenuation value above which an at least partial degree of contrast enhancement of a vessel is possible. The remaining vessels that are imaged by the image elements of the minimum image and were not identified as uncontrasted vessels may also be identified in step S2.2) as potentially contrasted vessels. Accordingly, the image elements of the minimum image that image the potentially contrasted vessels, may have an image value above the contrast threshold value.

In step S2.3), the uncontrasted vessels, that were identified in step S2.2), may be masked in the static mask image. The masking of the uncontrasted vessels in the static mask image may include for example a multiplication and/or subtraction of image values. It is possible to mask, for example remove, contributions of the uncontrasted vessels identified in step S2.2) to the static mask image. Thus, after step S2.3), the static mask image now contains only contributions of vessels that were identified in step S2.2) as potentially contrasted.

In step S2.4,) the uncontrasted vessels may be annotated in the dynamic mask image. The annotation of the uncontrasted vessels may in this case be performed analogously to the annotation in step S4.3).

The identification of the uncontrasted vessels by the minimum image provides a computationally efficient reduction of the unmasked image areas in the static mask image and of the unmasked image areas to be identified in the dynamic mask image. Steps S2.1) to S2.4) may be performed after step S1.3) and before step S3). Furthermore, steps S2.1) to S5) may be performed repeatedly until the abort condition occurs. In this case the projection images from step S5) may be provided for the purpose of determining the minimum image in step S2.1). Analogously thereto, the static mask image from step S4.2) and the dynamic mask image from step S4.3) may be provided for step S2.3) and step S2.4) respectively.

By giving precedence to steps S2.1) to S2.4), that may be performed with low computational overhead, it is possible to reduce a computational overhead for the following steps S3) to S5).

In an embodiment of the computer-implemented method for providing a dynamic mask image, an image-element-by-image-element minimum of backprojections of the projection images may be ascertained for the purpose of determining the minimum image in step S2.1). The image elements of the minimum image may be determined for example as points of intersection of the backprojection of the image elements of the projection images along the respective projection directions. In this case the image values of the image elements of the minimum image may be determined as a minimum of the image values of the backprojected image elements of the projection images. It may be ensured that a vessel that is imaged by an image element of the minimum image, the image value of the image element lying below the contrast threshold value, is imaged in at least one of the projection images by an image element whose image value likewise lies below the contrast threshold value. Consequently, there may be no overlapping with a contrasted vessel in the examination region along the projection direction of an image element of the projection image including an image value that lies below the contrast threshold value.

The embodiment variant provides a computationally efficient and at the same time reliable identification of a degree of contrast enhancement of the at least one vessel.

In an embodiment variant of the computer-implemented method for providing a dynamic mask image, at least two projection images, the projection directions of which extend substantially perpendicularly to one another, may be received in step S1.2). The at least two projection images may image the examination region at the same acquisition time point. The at least two projection images may be acquired and provided by a medical biplane X-ray device, for example. Because the projection directions of the at least two projection images extend substantially perpendicularly to one another, for example at an angle of 90 degrees, each image element of a first projection image may be assigned depth information by the second projection image. The substantially perpendicular course of the at least two projection directions provides a precise three-dimensional resolution of the examination region, for example of the at least one vessel, by the at least two projection images.

In an embodiment variant of the computer-implemented method for providing a dynamic mask image, step S3) may be based on an application of a ray tracing algorithm. In order to determine the exclusive rays in step S3), it is possible to trace rays, for example virtual rays, starting from the image elements of the projection images, the rays in each case extending in a ray incidence direction with respect to one of the projection directions. The ray tracing algorithm may be configured to discover a number of unmasked image areas in the static mask image along the ray that is to be traced in each case. If precisely one, for example cohesive, unmasked image area is discovered along one of the rays, the ray may be determined as an exclusive ray.

The image value of the image element from which the exclusive ray is emitted may be based on precisely one vessel and/or vessel segment that is imaged by the, for example cohesive, unmasked image area of the static mask image. Thus, an overlaying of portions of a plurality of vessels and/or vessel segments along an exclusive ray may be ruled out. Consequently, the degree of contrast enhancement of the vessel, for example of the unmasked image area by which the vessel is imaged, along the exclusive ray may be inferred based on an image value whose image element is a starting point of one of the exclusive rays.

In an embodiment of the computer-implemented method for providing a dynamic mask image, the abort condition may occur if the static mask image contains no unmasked image areas or no exclusive rays may be determined in step S3).

If the static mask image contains no unmasked image areas, the at least one unmasked image area that imaged the at least one vessel has been masked in step S2.3) and/or in step S4.2). Consequently, it is possible to identify the degree of contrast enhancement of the at least one vessel in step S2.2) and/or in step S4.1). In this case there remain no vessels that are imaged by an unmasked image area in the static mask image whose degree of contrast enhancement would require to be identified for the dynamic mask image. Accordingly, the repeated execution of steps S3) to S5), for example steps S2.1) to S5), may be aborted and the, for example most recently annotated, dynamic mask image may be provided.

If no exclusive rays may be determined in step S3), the repeated execution of steps S3) to S5), for example steps S2.1) to S5), may be aborted and the, for example most recently annotated, mask image may be provided. If, in addition, the static mask image contains no unmasked image areas, the method may be terminated. The degree of contrast enhancement of the imaged vessels is identified, for example completely. If the static mask image contains at least one unmasked image area and no exclusive ray may be determined in step S3), the repeated execution of steps S3) to S5), for example steps S2.1) to S5), may be aborted. The degree of contrast enhancement of the at least one vessel that is imaged by the at least one unmasked image area remaining in the static mask image may in this case be estimated as potentially contrasted in step S2.2).

The proposed abort condition provides a reliable check to be made on the further applicability of the proposed method for example with regard to the identifiability of the degree of contrast enhancement of remaining vessels that may be imaged by unmasked image areas in the static mask image.

In an embodiment of the computer-implemented method for providing a dynamic mask image, the method may additionally include a step S6). In step S6), a consistency value in terms of a data consistency with the projection images may be determined in each case in respect of possible degrees of contrast enhancement of the at least one unmasked image area of the static mask image. Furthermore, step S6) may be performed when the static mask image contains at least one unmasked image area and no exclusive rays may be determined in step S3). Also, the at least one image area of the dynamic mask image corresponding to the at least one unmasked image area of the static mask image may be annotated with the consistency value corresponding to the highest data consistency in accordance with the degree of contrast enhancement.

Step S6) may be performed when the abort condition occurs and the static mask image additionally contains at least one unmasked image area. In step S6), the possible degrees of contrast enhancement, for example possible combinations of degrees of contrast enhancement, may be determined for the at least one unmasked image area of the static mask image.

Furthermore, a consistency value in terms of the data consistency with the projection images may be determined in each case for the possible degrees of contrast enhancement of the at least one unmasked image area of the static mask image. The consistency value may estimate the data consistency between the projection images and an image of the at least one unmasked image area having the respective degree of contrast enhancement.

If the static mask image in step S6) contains a number of unmasked image areas, the consistency values for the possible combinations of degrees of contrast enhancement of the unmasked image areas may be determined. Furthermore, the image areas of the dynamic mask image corresponding to the unmasked image areas of the static mask image may be annotated in accordance with the combination of degrees of contrast enhancement, which combination has the highest consistency value.

The unmasked image areas of the static mask image that cannot be identified in step S2.2) and/or S4.1) are identified. After step S6), all unmasked image areas of the dynamic mask image are annotated, uncontrasted or contrasted, according to the respective degree of contrast enhancement.

As the determination of the consistency values of the possible combinations of degrees of contrast enhancement for the at least one unmasked image area of the static mask image requires a comparatively high computational overhead, the computational overhead may be reduced by performing step S6) when the abort condition occurs, for example after the preceding computationally efficient method steps have been exhausted.

In a further advantageous embodiment variant of the proposed computer-implemented method for providing a dynamic mask image, step S6) may further include a generation of forward projections of the at least one unmasked image area of the static mask image along the projection directions. In this case the at least one consistency value may be based on a comparison between the projection images and the forward projections corresponding thereto.

At least two forward projections in each case of the at least one unmasked image area of the static mask image may be generated for one of the possible degrees of contrast enhancement in each case, for example for one combination in each case of the possible degrees of contrast enhancement, of the at least one unmasked image area of the static mask image. The forward projections may in this case have for example the same dimensionality and/or spatial resolution as the respective projection images along the same projection direction. This provides a comparison, for example image element by image element, between the forward projections and corresponding projection images in terms of the projection direction for the purpose of determining the consistency value. A high consistency value may be achieved for an extensive agreement, for example image element by image element, between forward projection and projection image corresponding thereto. The degree of contrast enhancement that is used on the basis of its consistency value for the annotation of the dynamic mask image in step S6) may also include a high data consistency with regard to the projection images.

In an embodiment of the computer-implemented method for providing a dynamic mask image, the masking of the identified vessels in the static mask image may include a subtraction of image values of the static mask image.

The at least one unmasked image area of the static mask image that images an identified vessel, may be converted into a masked image area of the static mask image. For example, the image values of the image elements of the at least one unmasked image area and/or a predetermined image value may be subtracted from the image values of the image elements of the same unmasked image area.

In an embodiment of the computer-implemented method for providing a dynamic mask image, the masking of the imaging of the contrasted vessels identified in step S4.1) in the projection images in step S5) may include a subtraction of image values of the projection images.

The forward projections of the at least one unmasked image area of the static mask image along the projection directions, for example image element by image element, may be subtracted from the projection images. This provides portions of image values of the image elements of the projection images that are based on a forward projection of the at least one unmasked image area to be removed from the projection images, following the identification of the unmasked image area. Furthermore, portions of image values of the image elements of the projection images of further unmasked image areas of the static mask image that have thus far not been identified, may continue to be retained in the projection images. Thus, with each repeated execution of steps S3) to S5), for example steps S2.1) to S5), the static mask image, the dynamic mask image and the projection images may be updated, for example masked and/or annotated, in accordance with the respective already identified degree of contrast enhancement of the at least one vessel imaged therein. A high data consistency between the static mask image masked in step S4.2), the dynamic mask image annotated in step S4.3) and the projection images masked in step S5) may be provided, for example for the respective following iteration. Since the determination of the exclusive rays in step S3) is based both on the static mask image and on the most recently provided projection images in each case, a determination of possible further exclusive rays in step S3) of the respective following iteration may be provided.

Embodiments also include a provisioning unit including a computing unit, a memory unit and an interface. The provisioning unit is configured for performing the above-described methods for providing a dynamic mask image and their aspects. The provisioning unit is configured to perform the methods and their aspects to the extent that the interface, the memory unit and the computing unit are configured to perform the corresponding method steps.

The interface may be configured for performing steps S1.1) to S1.2) and S7) of the proposed method. Furthermore, the computing unit and/or the memory unit may be configured for performing steps S3) to S5), for example steps S2.1) to S6), of the proposed method.

The advantages of the proposed provisioning unit substantially correspond to the advantages of the proposed computer-implemented method for providing a dynamic mask image. Features, advantages or alternative embodiment variants mentioned in this context may equally be applied also to the other claimed subject matters, and vice versa.

Embodiments provide a medical imaging device including a proposed provisioning unit. The medical imaging device, for example the provisioning unit, is in this case configured for performing a proposed computer-implemented method for providing a dynamic mask image. For example, the medical imaging device may be configured as a medical X-ray device, for example a biplane X-ray device, and/or as a computed tomography (CT) system and/or as an ultrasound device and/or as a positron emission tomography (PET) system. At the same time the medical imaging device may also be configured for acquiring and/or receiving and/or providing the projection images and/or the static mask image.

The advantages of the proposed medical imaging device substantially correspond to the advantages of the proposed computer-implemented method for providing a dynamic mask image. Features, advantages or alternative embodiment variants mentioned in this context may equally be applied also to the other claimed subject matters, and vice versa.

Embodiments provide a computer program product including a computer program that may be loaded directly into a memory of a provisioning unit and includes program sections for performing all steps of the proposed method for providing a dynamic mask image when the program sections are executed by the provisioning unit. The computer program product may in this case include software including a source code that still needs to be compiled and linked or that only needs to be interpreted, or an executable software code that only has to be loaded into the provisioning unit in order to execute. The computer program product provides the method for providing a dynamic mask image by a provisioning unit to be performed quickly in an identically repeatable and robust manner. The computer program product is configured in such a way that it may perform the method steps by the provisioning unit.

The computer program product is stored for example on a computer-readable storage medium or is resident on a network or server from where it may be loaded into the processor of a provisioning unit that is directly connected to the provisioning unit or may be configured as part of the provisioning unit. In addition, control information of the computer program product may be stored on an electronically readable data medium. The control information of the electronically readable data medium may be configured in such a way that it performs the steps of the method when the data medium is used in a provisioning unit. Examples of electronically readable data media are a DVD, a magnetic tape or a USB stick on which electronically readable control information, for example software, is stored. When the control information is read from the data medium and stored in a provisioning unit, all embodiments of the previously described methods may be performed.

Embodiments may be based on or include a computer-readable storage medium and/or electronically readable data medium on which program sections that may be read and executed by a provisioning unit are stored in order to perform all steps of the method for providing a dynamic mask image when the program sections are executed by the provisioning unit.

A software-based implementation includes an advantage that provisioning units already used previously may also be easily upgraded by a software update in order to operate in the manner. In addition to the computer program, such a computer program product may where appropriate include additional constituent parts such as e.g., a set of documentation and/or additional components, as well as hardware components, such as e.g., hardware keys (dongles, etc.) to provide use of the software.

DETAILED DESCRIPTION

Figure 1:
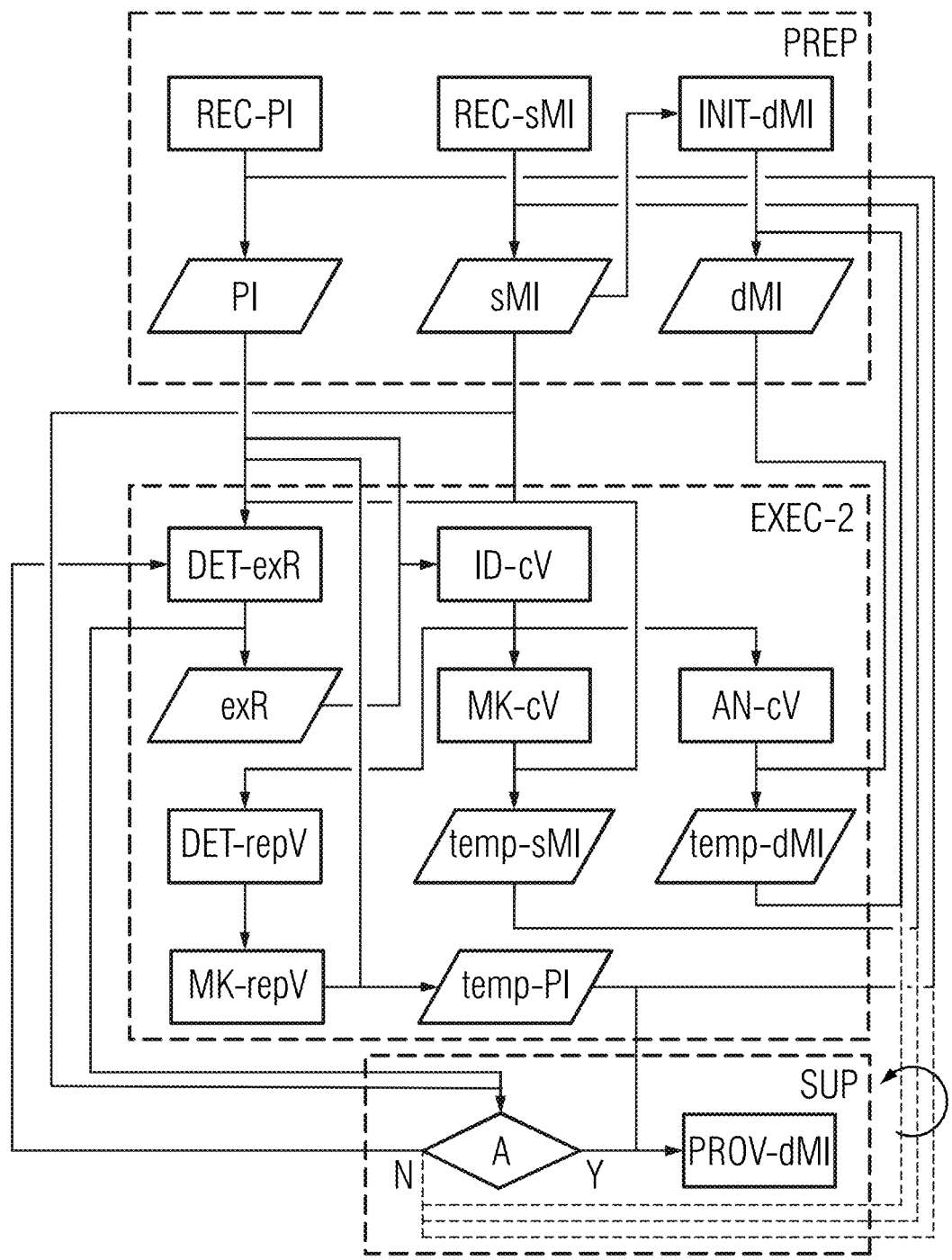
FIGS. 1, 2, and 3 depict schematic representations of different embodiments of a method for providing a dynamic mask image.

FIG. 1 depicts a schematic representation of an embodiment of the method for providing a dynamic mask image. In a first step S1.1), projection images PI of an examination region of an examination subject are received REC-PI. The projection images PI may image the examination region from at least two different projection directions. In a second step S1.2), a static mask image sMI may be received REc-sMI. Furthermore, the examination region may contain at least one vessel that is imaged by an unmasked image area of the static mask image sMI. In a third step S1.3), the dynamic mask image dMI may be initialized INIT-dMI by the static mask image sMI. The above-described steps S1.1) to S1.3) may be regarded for example as a preparation phase PREP of the proposed method. In a further step S3), exclusive rays exR may be determined DET-exR. Each of the exclusive rays exR may extend in a ray incidence direction with respect to one of the projection directions and correspond to a respective image value in the associated projection image PI. Furthermore, at least one of the exclusive rays exR may extend in each case through precisely one of the unmasked image areas of the static mask image sMI. After this, in a step S4.1), contrasted and uncontrasted vessels may be identified ID-cV based on the corresponding image value in each case. In a further step S4.2), the vessels identified in step S4.1) may be masked MK-cV in the static mask image sMI. Also, in a step S4.3), the contrasted and uncontrasted vessels may be annotated AN-cV in the dynamic mask image dMI. An imaging of the contrasted vessels identified in step S4.1) may be determined DET-repV and masked MK-repV in the projection images. The above-described steps S3) to S5) may be regarded in this case as a calculation phase EXEC-2. Furthermore, steps S3) to S5) of the calculation phase EXEC-2 may be performed repeatedly until an abort condition A occurs. In this case the, for example most recently, masked static mask image temp-sMI may be provided as the static mask image sMI for the following iteration. Analogously thereto, the, for example most recently, masked projection images temp-PI and the, for example most recently, annotated dynamic mask image temp-dMI may be provided as the projection images PI or the dynamic mask image dMI for the respective following iteration. If the abort condition A occurs, the, for example most recently, annotated dynamic mask image temp-dMI may be provided PROV-dMI in a step S7). Step S7) may be considered in this context for example as a provisioning phase SUP of the proposed method.

In step S1.2), at least two projection images PI may be received REC-PI whose projection directions extend substantially perpendicularly to one another.

Furthermore, the determination of the exclusive rays DET-exR in step S3) may be based on an application of a ray tracing algorithm.

The abort condition A may occur when the static mask image sMI has no unmasked image areas or no exclusive rays exR may be determined in step S3).

Figure 2:
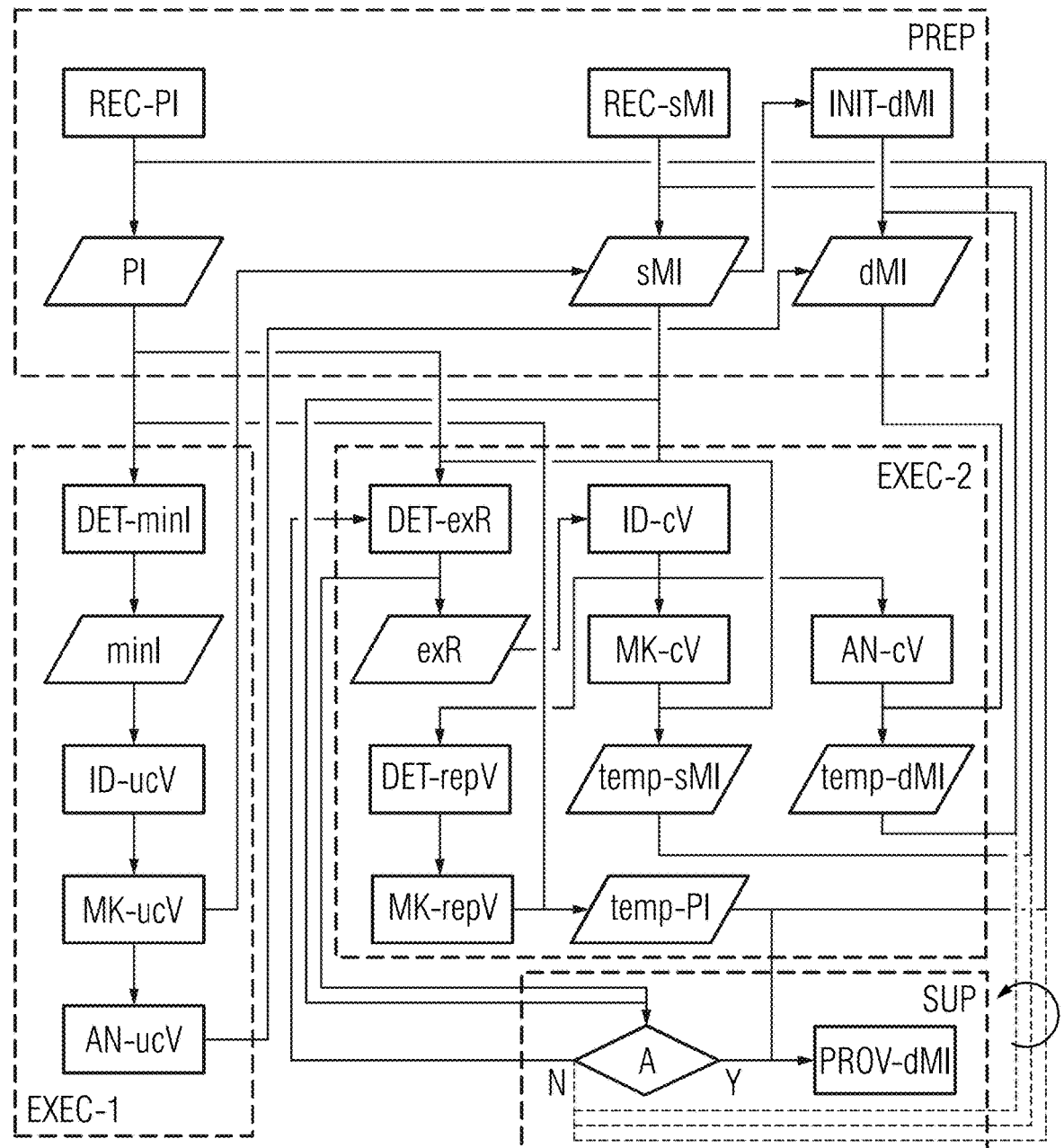

FIG. 2 depicts a schematic representation of an embodiment variant of the method for providing a dynamic mask image PROV-dMI. In this case the method may additionally include a step S2.1) in which a minimum image minI is determined DET-minI based on the projection images PI. In order to determine the minimum image DET-minI, a minimum of backprojections of the projection images PI may be ascertained image element by image element. After this, in a step S2.2), uncontrasted and potentially contrasted vessels may be identified ID-ucV in the minimum image minI. Furthermore, in a further step S2.3), the uncontrasted vessels may be masked in the static mask image sMI. In addition, in a step S2.4), the uncontrasted vessels may be annotated AN-ucV in the dynamic mask image dMI. In this case steps S2.1) to S2.4) may be regarded as a further calculation phase EXEC-1 of the method. The further calculation phase EXEC-1 may be executed after the preparation phase PREP and before the calculation phase EXEC-2. For example, the two calculation phases EXEC-1 and EXEC-2 may be executed repeatedly until the abort condition A occurs.

Figure 3:
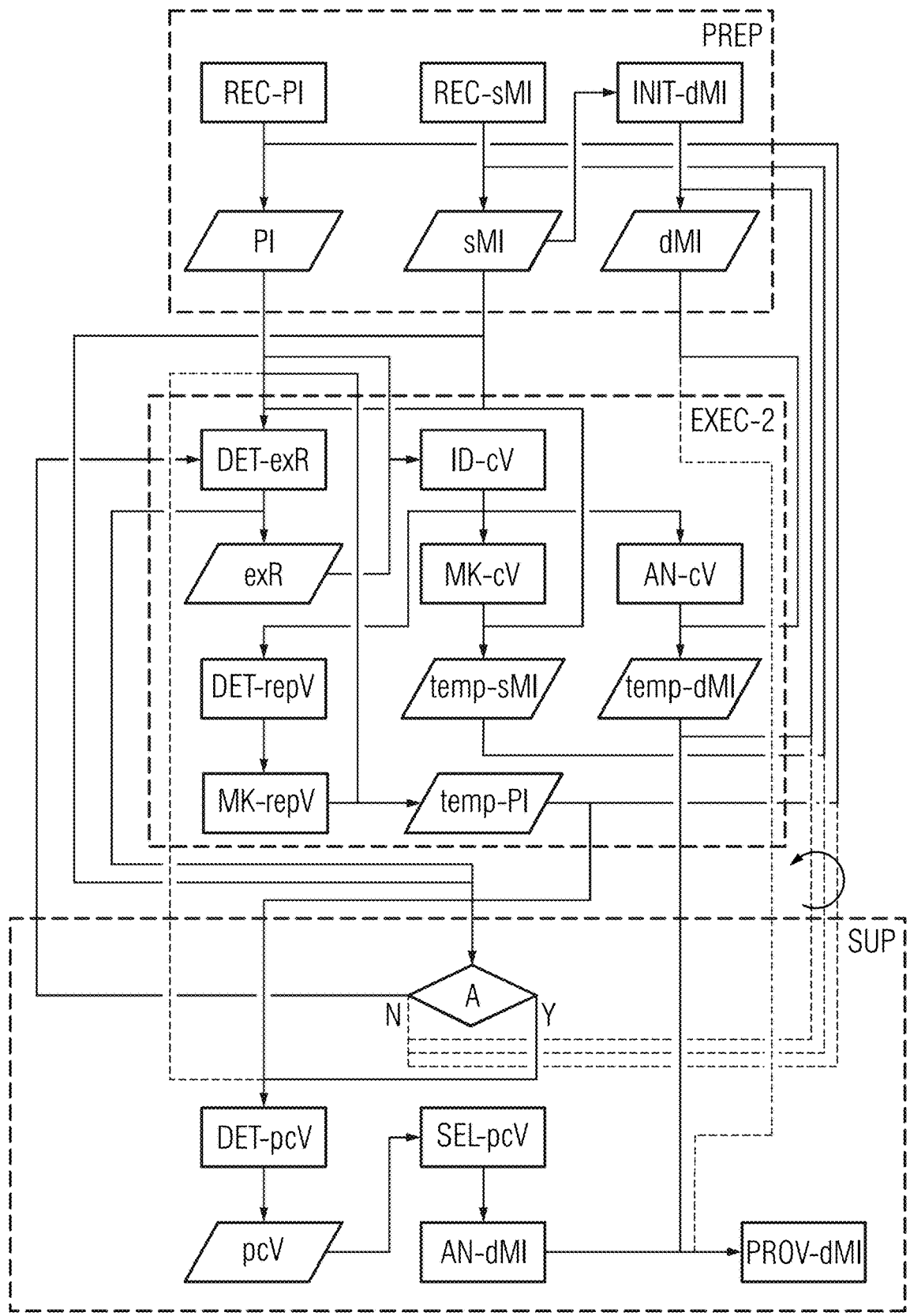

A further embodiment of the method for providing a dynamic mask image PROV-dMI is represented schematically in FIG. 3. In this case the proposed method, for example the provisioning phase SUP, may include a further step S6). In step S6), a consistency value pcV relating in each case to possible degrees of contrast enhancement of the at least one unmasked image area of the static mask image sMI may be determined DET-pcV with regard to a data consistency with the projection images PI. For this purpose, for example forward projections of the at least one unmasked image area of the static mask image sMI may be generated along the projection directions. The at least one consistency value pcV may be based in this case on a comparison between the projection images PI and the forward projections corresponding thereto. Step S6) may be performed when the static mask image sMI has at least one unmasked image area and no exclusive rays exR may be determined in step S3). Furthermore, the optimal degree of contrast enhancement of the at least one unmasked image area of the static mask image sMI may be determined SEL-pcV on the basis of the consistency value pcV, which consistency value pcV corresponds to the highest data consistency. After this, the image area of the dynamic mask image dMI corresponding to the at least one unmasked image area of the static mask image sMI may be annotated AN-dMI with the consistency value corresponding to the highest data consistency in accordance with the degree of contrast enhancement.

The determination of the consistency values pcV associated with the possible degrees of contrast enhancement of a number n of unmasked image areas UM remaining in the static mask image sMI in step S6) may include for example a determination of all $2^{|n|}$ combinations of degrees of contrast enhancement. In this case each of the vessels may be contrasted, for example filled with a contrast agent, or contrasted, for example unfilled.

Figure 4:
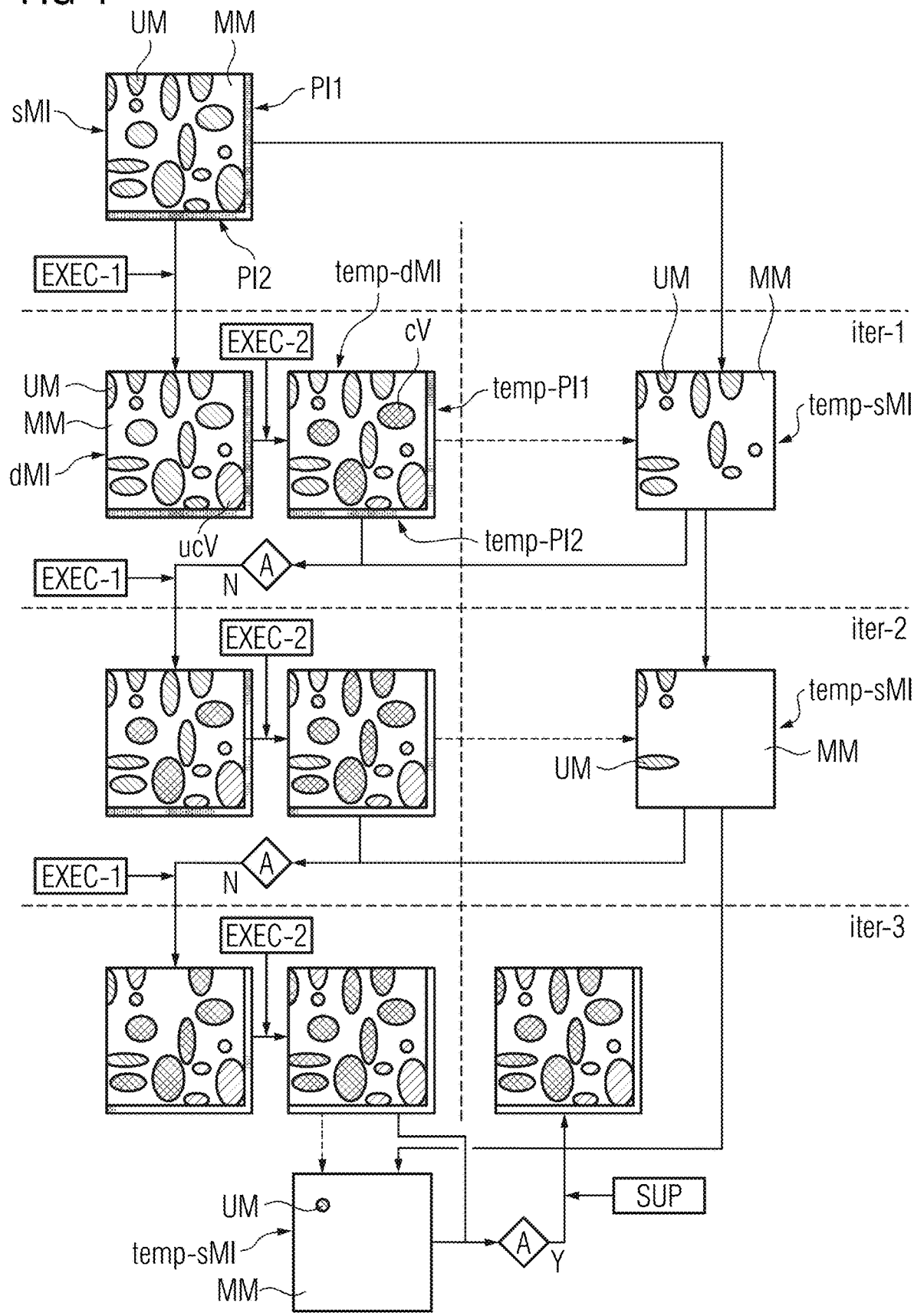
FIG. 4 depicts a schematic representation of a data flow according to an embodiment of the proposed method for providing a dynamic mask image.

FIG. 4 depicts a schematic representation of a data flow in the case of an embodiment variant of the proposed method for providing a dynamic mask image PROV-dMI. Here, for example two projection images PI1 and PI2 whose projection directions extend perpendicularly to one another may be received REC-PI during the preparation phase. Furthermore, the examination region that is imaged in the projection images PI1 and PI2 may contain a plurality of vessels. Furthermore, the static mask image sMI may be generated and/or received REC-sMI based on the projection images PI1 and PI2. The static mask image sMI may contain several unmasked image areas UM, by which unmasked image areas UM the vessels of the examination region are imaged. Furthermore, the remaining part of the static mask image sMI may be masked MM. In FIG. 4, the static mask image is depicted as two-dimensional by way of example and the projection images PI1 and PI2 are each represented as one-dimensional. Furthermore, the dynamic mask image dMI may be initialized by specification of the static mask image sMI. The image values of the projection images PI1 and PI2 are illustrated schematically here by crosshatching. A tighter crosshatching illustrates an image value by way of example, which image value corresponds to a higher degree of contrast enhancement of the section of the examination region imaged therein.

The calculation phases EXEC-1 and EXEC-2 may be executed one after the other in a first iteration iter-1. Following the first execution of the further calculation phase EXEC-1, uncontrasted vessels ucV may be identified ID-ucV and annotated AN-ucV in the dynamic mask image dMI. After a first execution of the calculation phase EXEC-2, contrasted vessels cV may be identified ID-cV by determining the exclusive rays exR and annotated AN-dMI in the dynamic mask image dMI. Furthermore, an imaging of the identified contrasted vessels cV may be determined DET-repV and masked MK-repV in the projection images PI1 and PI2. The masking of the imaging of the identified contrasted vessels in the projection images PI1 and PI2 may in this case include a subtraction of image values of the projection images PI1 and PI2.

Following the first iteration iter-1, the abort condition A may be checked. Because the static mask image sMI still contains unmasked image areas UM, steps S2.1) to S5) may be performed repeatedly. The masking of the identified vessels in the static mask image sMI may include a subtraction of image values of the static mask image sMI. In the exemplary embodiment illustrated in FIG. 4, the static mask image contains four unmasked image areas UM after the second iteration iter-2 and one unmasked image area UM after the third iteration iter-3. If no exclusive ray exR may be determined for the remaining unmasked image area UM in the, for example most recently, masked static mask image temp-sMI after the third iteration iter-3, the abort condition A may occur Y. After this, the degree of contrast enhancement of the vessel that is imaged by the remaining unmasked image area UM of the static mask image temp-sMI may be determined SEL-pcV, that has the highest consistency value pcV. Furthermore, the image area of the dynamic mask image temp-dMI corresponding to the remaining unmasked image area UM of the static mask image temp-sMI may be annotated AN-dMI with the highest consistency value pcV in accordance with the degree of contrast enhancement. After this, the, for example most recently, annotated dynamic mask image dMI may be provided PROV-dMI.

Figure 5:
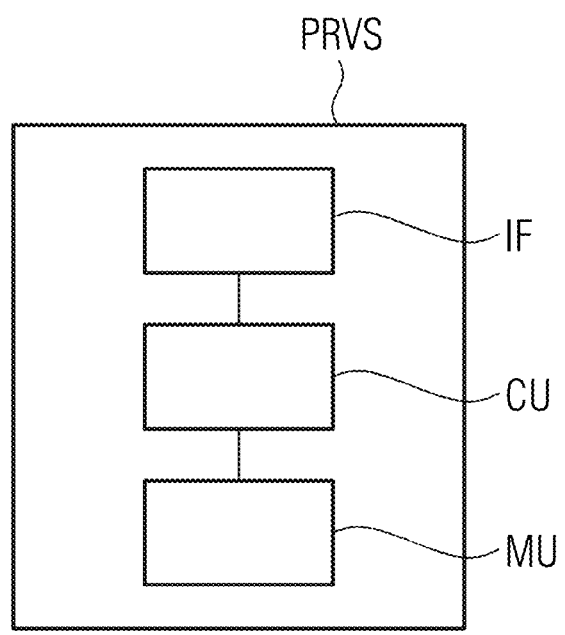
FIG. 5 depicts a schematic representation of a provisioning unit according to an embodiment.

FIG. 5 schematically illustrates a proposed provisioning unit PRVS including an interface IF, a computing unit CU and a memory unit MU. The provisioning unit PRVS may be configured for performing a proposed method for providing a dynamic mask image PROV-dMI to the extent that the interface IF, the computing unit CU and the memory unit MU are configured to perform the corresponding method steps.

The interface IF may be configured for performing steps S1.1) to S1.2) and S7) of the proposed method. Furthermore, the computing unit CU and/or the memory unit MU may be configured for performing steps S3) to S5), for example steps S2.1) to S6), of the method.

The provisioning unit PRVS may be for example a computer, a microcontroller or an integrated circuit. Alternatively, the provisioning unit PRVS may be a real or virtual network of interconnected computers (a technical term for a real network is "cluster"; a technical term for a virtual network is "cloud"). The provisioning unit PRVS may also be configured as a virtual system that is implemented on a real computer or a real or virtual network of interconnected computers (virtualization).

An interface IF may be a hardware or software interface (for example PCI bus, USB or Firewire). A computing unit CU may include hardware elements or software elements, for example a microprocessor or an FPGA (acronym for Field Programmable Gate Array). A memory unit MU may be realized as a volatile working memory known as RAM (Random Access Memory) or as a nonvolatile mass storage device (hard disk, USB stick, SD card, SSD (Solid State Disk)).

The interface IF may for example include a number of sub-interfaces that perform different steps of the respective methods. In other words, the interface IF may also be understood as a plurality of interfaces IF. The computing unit CU may for example include a number of sub-computing units that perform different steps of the respective methods. In other words, the computing unit CU may also be understood as a plurality of computing units CU.

Figure 6:
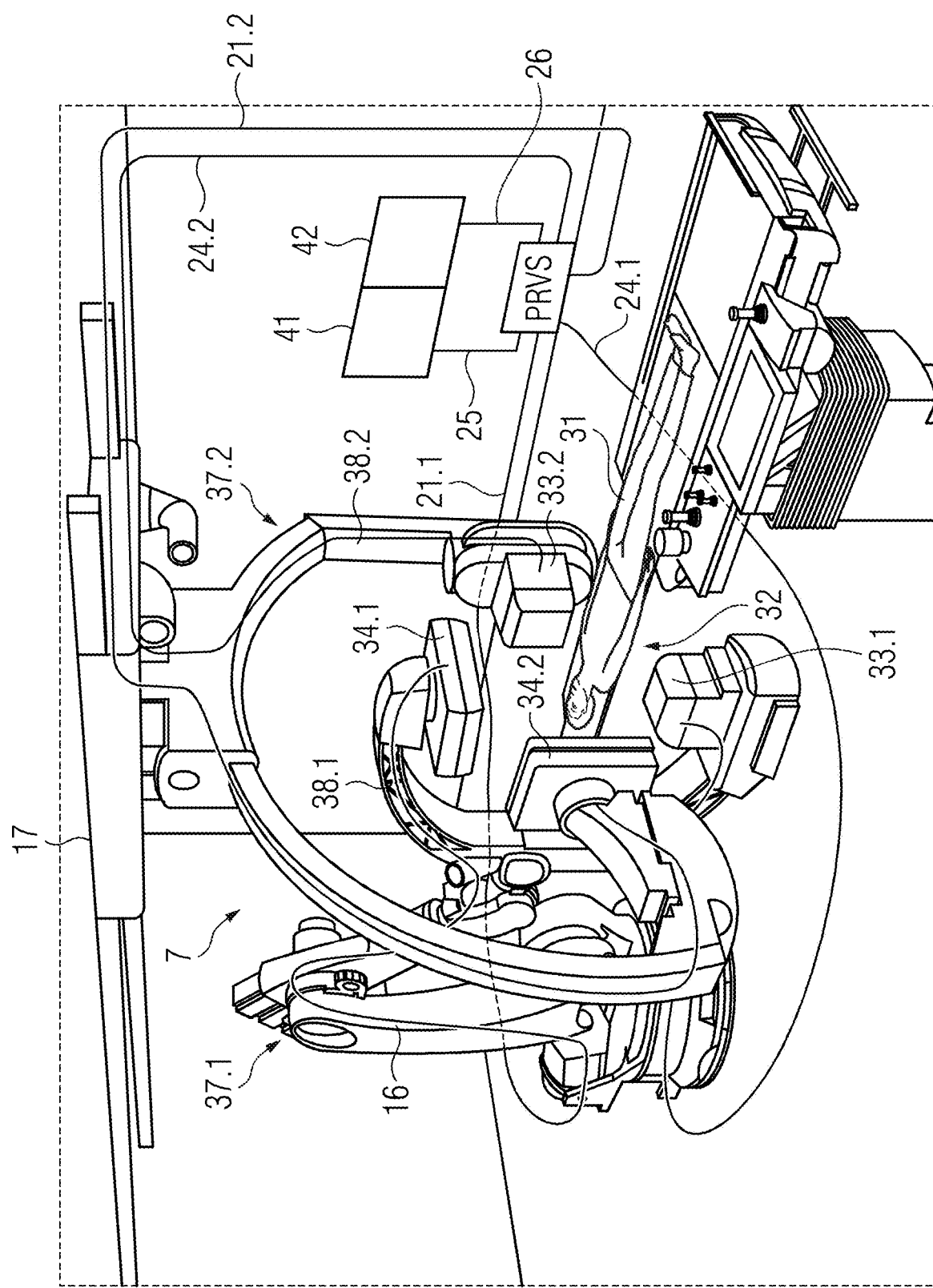
FIG. 6 depicts a schematic representation of a medical biplane X-ray device.

FIG. 6 illustrates a biplane X-ray device 7 by way of example for a medical imaging device. Here, the biplane X-ray device 7 includes a first X-ray image acquisition apparatus 37.1 and a second X-ray image acquisition apparatus 37.2. The first X-ray image acquisition apparatus 37.1 includes for example a 6-axis articulated-arm robot 16 to which is attached a C-arm 38.1 carrying an X-ray source 33.1 and an X-ray detector 34.1. In the embodiment, the second X-ray image acquisition apparatus 37.2 includes a traveling rail-mounted stand 17 that carries a movable C-arm 38.2 on which a further X-ray source 33.2 and a further X-ray detector 34.2 are mounted.

The medical biplane X-ray device 7 may include a proposed provisioning unit PRVS. Furthermore, the biplane X-ray device 7, for example the proposed provisioning unit PRVS, is configured for performing a proposed method for providing a dynamic mask image PROV-dMI.

For the purpose of acquiring the projection images PI, the C-arm 38.1 of the first X-ray image acquisition apparatus 37.1 and the C-arm 38.2 of the second X-ray image acquisition apparatus 37.2 may each be mounted so as to be movable about one or more axes.

For the purpose of acquiring the projection images PI of the examination region of the examination subject 31 disposed on a patient support and positioning apparatus 32, the provisioning unit PRVS may send a signal 24.1 and 24.2 to the first 33.1 and the further X-ray source 33.2. The X-ray source 33.1 may thereupon transmit a first X-ray pencil of rays, for example a cone beam and/or fan beam and/or parallel ray, along a first projection direction, for example a first ray incidence direction. When the first X-ray pencil of rays, following an interaction with the examination region of the examination subject 31 that is to be imaged, is incident on a surface of the X-ray detector 34.1, the X-ray detector 34.1 may send a signal 21.1 to the provisioning unit PRVS. Analogously thereto, the further X-ray source 33.2 may transmit a further X-ray pencil of rays along a further projection direction, which further projection direction is different from the first projection. When the further X-ray pencil of rays, following an interaction with the examination region of the examination subject 31 that is to be imaged, is incident on a surface of the further X-ray detector 34.2, the further X-ray detector 34.2 may send a further signal 21.2 to the provisioning unit PRVS. The provisioning unit PRVS may for example reconstruct and/or receive the projection images on the basis of the signal 21.1 and the further signal 21.2.

In this case the biplane X-ray device 7, for example the angled arrangement of the first 37.1 and second X-ray image acquisition apparatus 37.2 relative to one another, enables an, for example simultaneous, acquisition of at least two projection images PI1 and PI2 in each case from different projection directions.

Furthermore, the medical biplane X-ray device 7 may include an input unit 42, for example a keyboard, and/or a visualization unit 41, for example a monitor and/or display. The input unit 42 may preferably be integrated into the visualization unit 41, for example in the case of a capacitive and/or resistive input display. In this case it is possible for the medical biplane X-ray device 7, for example the method for providing a dynamic mask image PROV-dMI, to be controlled by an input by a user at the input unit 42.

Furthermore, the visualization unit 41 may be configured to display information and/or graphical representations of information of the medical biplane X-ray device 7 and/or of the provisioning unit PRVS and/or of further components. For this purpose, the provisioning unit PRVS may for example send a signal 25 to the visualization unit 41. For example, the visualization unit 41 may be further configured for displaying a graphical representation of the static mask image sMI and/or of the projection images PI and/or of the dynamic mask image dMI and/or of the minimum image minI.

The schematic representations contained in the described figures do not reflect a scale or proportions of any kind.

The methods described in detail in the foregoing, as well as the illustrated facilities, are embodiments that may be modified in the most diverse ways by the person skilled in the art without leaving the scope of the invention. Furthermore, the use of the indefinite articles "a" or "an" does not exclude the possibility that the features in question may also be present more than once. Similarly, the terms "unit" and "element" do not rule out the possibility that the components in question consist of a plurality of cooperating subcomponents, that if necessary, may also be distributed in space.

It is to be understood that the elements and features recited in the appended claims may be combined in different ways to produce new claims that likewise fall within the scope of the present invention. Thus, whereas the dependent claims appended below depend from only a single independent or dependent claim, it is to be understood that these dependent claims may, alternatively, be made to depend in the alternative from any preceding or following claim, whether independent or dependent, and that such new combinations are to be understood as forming a part of the present specification.

While the present invention has been described above by reference to various embodiments, it may be understood that many changes and modifications may be made to the described embodiments. It is therefore intended that the foregoing description be regarded as illustrative rather than limiting, and that it be understood that all equivalents and/or combinations of embodiments are intended to be included in this description.

The invention claimed is:

1. A computer-implemented method for providing a dynamic mask image, the method comprising:
   receiving projection images of an examination region of an examination subject, wherein the projection images image the examination region from at least two different projection directions;
   receiving a static mask image, wherein the examination region contains at least one vessel that is imaged by an unmasked image area of the static mask image;
   initializing the dynamic mask image by the static mask image;
   determining one or more exclusive rays, wherein each of the one or more exclusive rays extend in a ray incidence direction of one of the at least two different projection directions and correspond to a respective image value in an associated projection image and wherein the each of the one or more exclusive rays extend through precisely one of the unmasked image areas of the static mask image;
   identifying one or more contrasted vessels and uncontrasted vessels based on the corresponding image value;
   masking the one or more contrasted and uncontrasted vessels in the static mask image;
   annotating the one or more contrasted vessels and uncontrasted vessels in the dynamic mask image;
   determining and masking an imaging of the one or more contrasted vessels in the projection images;
   repeating determining, identifying, masking, annotating, determining and masking until an abort condition occurs; and
   providing the dynamic mask image.

2. The method of claim 1, further comprising prior to determining the one or more exclusive rays:
   determining a minimum image based on the projection images;
   identifying uncontrasted and potentially contrasted vessels in the minimum image;
   masking the uncontrasted vessels in the static mask image; and
   annotating the uncontrasted vessels in the dynamic mask image.

3. The method of claim 2, wherein a minimum of back-projections of the projection images are ascertained image element by image element to determine the minimum image.

4. The method of claim 1, wherein at least two projection images, the at least two different projection directions of which extend substantially perpendicular to one another, are received.

5. The method of claim 1, wherein determining the one or more exclusive rays comprises applying a ray tracing algorithm.

6. The method of claim 1, wherein the abort condition occurs when the static mask image contains no unmasked image areas or no exclusive rays are determined.

7. The method of claim 1, further comprising:
   determining, when the static mask image contains at least one unmasked image area and no exclusive rays may be determined, a consistency value in terms of a data consistency with the projection images in respect of possible degrees of contrast enhancement of the at least one unmasked image area of the static mask image;
   wherein the at least one image area of the dynamic mask image corresponding to the at least one unmasked image area of the static mask image is annotated with the consistency value corresponding to a highest data consistency in accordance with a degree of contrast enhancement.

8. The method as claimed in claim 7, wherein determining the consistency value comprises:
   generating forward projections of the at least one unmasked image area of the static mask image along at least two different projection directions;
   wherein the consistency value is based on a comparison between the projection images and corresponding forward projections thereto.

9. The method of claim 1, wherein the masking of the identified one or more contrasted vessels and uncontrasted vessels in the static mask image comprises a subtraction of image values of the static mask image.

10. The method of claim 1, wherein the masking of the imaging of the contrasted vessels identified in the projection images comprises a subtraction of image values of the projection images.

11. A provisioning unit for providing a dynamic mask image, the provisioning unit comprising:
    a processor; and
    a memory coupled to the processor, the memory configured to store machine-readable instructions executable by the processor, the machine-readable instructions comprising instructions to:
    receive projection images of an examination region of an examination subject, wherein the projection images image the examination region from at least two different projection directions;
    receive a static mask image, wherein the examination region contains at least one vessel that is imaged by an unmasked image area of the static mask image;
    initialize the dynamic mask image by the static mask image;
    determine one or more exclusive rays, wherein each of the one or more exclusive rays extend in a ray incidence direction of one of the at least two different projection directions and correspond to a respective image value in an associated projection image and wherein the each of the one or more exclusive rays extend through precisely one of the unmasked image areas of the static mask image;
    identify one or more contrasted and uncontrasted vessels based on the corresponding image value;
    mask the one or more contrasted and uncontrasted vessels in the static mask image;

annotate the one or more contrasted and uncontrasted vessels in the dynamic mask image;

determine and mask an imaging of the one or more contrasted vessels in the projection images;

repeat determining, identifying, masking, annotating, determining and masking until an abort condition occurs; and provide the dynamic mask image.

12. The provisioning unit of claim 11, further comprising a medical imaging device configured for acquiring and/or receiving and/or providing the projection images and/or the static mask image.

13. The provisioning unit of claim 11, wherein the machine-readable instructions further comprise instructions to prior to determining the one or more exclusive rays:

determine a minimum image based on the projection images;

identify uncontrasted and potentially contrasted vessels in the minimum image;

mask the uncontrasted vessels in the static mask image; and annotate the uncontrasted vessels in the dynamic mask image.

14. The provisioning unit of claim 13, wherein a minimum of backprojections of the projection images are ascertained image element by image element to determine the minimum image.

15. The provisioning unit of claim 11, wherein at least two projection images, at least two different projection directions of which extend substantially perpendicular to one another, are received.

16. The provisioning unit of claim 11, wherein determining the one or more exclusive rays comprises applying a ray tracing algorithm.

17. The provisioning unit of claim 11, wherein the abort condition occurs when the static mask image contains no unmasked image areas or no exclusive rays are determined.

18. The provisioning unit of claim 11, wherein the machine-readable instructions further comprise instructions to:

determine, when the static mask image contains at least one unmasked image area and no exclusive rays may be determined, a consistency value in terms of a data consistency with the projection images in respect of possible degrees of contrast enhancement of the at least one unmasked image area of the static mask image;

wherein the at least one image area of the dynamic mask image corresponding to the at least one unmasked image area of the static mask image is annotated with the consistency value corresponding to a highest data consistency in accordance with a degree of contrast enhancement.

19. The provisioning unit of claim 18, wherein the instructions to determine the consistency value comprise instructions to:

generate forward projections of the at least one unmasked image area of the static mask image along the at least two different projection directions;

wherein the consistency value is based on a comparison between the projection images and the forward projections corresponding thereto.

20. The provisioning unit of claim 11, wherein the masking of the identified one or more contrasted vessels and uncontrasted vessels in the static mask image comprises a subtraction of image values of the static mask image.

* * * * *